(12) United States Patent
Banning

(10) Patent No.: US 7,636,977 B2
(45) Date of Patent: Dec. 29, 2009

(54) TOPPER FOR POWER TOOTHBRUSH AND METHOD FOR FORMING THE SAME

(75) Inventor: Robert D. Banning, St. Louis, MO (US)

(73) Assignee: The Gillette Company, Cincinnati, OH (US)

( * ) Notice: Subject to any disclaimer, the term of this patent is extended or adjusted under 35 U.S.C. 154(b) by 0 days.

(21) Appl. No.: 11/511,747

(22) Filed: Aug. 29, 2006

(65) Prior Publication Data
US 2006/0288504 A1 Dec. 28, 2006

Related U.S. Application Data

(63) Continuation of application No. 10/237,902, filed on Sep. 9, 2002, now abandoned.

(51) Int. Cl.
*A61C 17/22* (2006.01)
(52) U.S. Cl. .......................... 15/22.1; 15/246; 15/167.1
(58) Field of Classification Search .................. 15/22.1, 15/22.2, 167.1, 246, 21.1
See application file for complete search history.

(56) References Cited

U.S. PATENT DOCUMENTS

| | | |
|---|---|---|
| 3,220,543 A | 11/1965 | McCord et al. |
| 3,533,503 A | 10/1970 | Wood et al. |
| D237,659 S | 11/1975 | Meyer et al. |
| 5,068,939 A | 12/1991 | Holland |
| 5,187,829 A | 2/1993 | Atkins |
| D341,943 S | 12/1993 | Si-Hoe |
| 5,435,034 A * | 7/1995 | Bigler et al. ................. 15/22.1 |
| D368,373 S | 4/1996 | Shimatsu et al. |
| 5,774,921 A | 7/1998 | Harrison et al. |

(Continued)

FOREIGN PATENT DOCUMENTS

CA 81887 9/1997

(Continued)

OTHER PUBLICATIONS

Office Action for U.S. Appl. No. 10/237,902; dated Mar. 30, 2006.

(Continued)

*Primary Examiner*—Shay L Karls
(74) *Attorney, Agent, or Firm*—Vladimir Vitenberg; George H. Leal; James C. Vago

(57) ABSTRACT

A decorative piece in the form of a topper designed to seat at the base of the shaft and extending from the handle body of a powered toothbrush is provided. The topper is formed as a single molded piece on top of a base ring having a central hole that fits over the shaft and a lower skirt that mates with the handle. The base ring includes grooves or other indentations about the central hole that receive inflow from the topper when it is molded. According to one embodiment, to construct the topper, the base ring is held in place with respect to the topper mold and molten or otherwise-liquid plastic is injected into the mold so that it fills the mold cavity and thereby flows into the indentations in the base ring, thereby securing the topper to the base ring when the decorative feature hardens sufficiently. The base ring and topper can then be slid over the shaft into a final mounted position on the assembled brush.

8 Claims, 5 Drawing Sheets

U.S. PATENT DOCUMENTS

| | | | |
|---|---|---|---|
| D416,686 S | 11/1999 | Meeker et al. | |
| 6,000,083 A | 12/1999 | Blaustein et al. | |
| 6,015,328 A | 1/2000 | Glaser | |
| D428,258 S | 7/2000 | Moskovich et al. | |
| D428,259 S | 7/2000 | Moskovich et al. | |
| 6,102,203 A | 8/2000 | Marro | |
| 6,141,815 A | 11/2000 | Harrison et al. | |
| 6,189,693 B1 | 2/2001 | Blaustein et al. | |
| 6,202,242 B1 * | 3/2001 | Salmon et al. | 15/22.1 |
| D452,380 S | 12/2001 | Cheong et al. | |
| 6,360,395 B2 | 3/2002 | Blaustein et al. | |
| 6,371,294 B1 | 4/2002 | Blaustein et al. | |
| 6,467,119 B1 * | 10/2002 | Van Meter et al. | 15/22.1 |
| 6,579,395 B1 * | 6/2003 | Smith | 156/89.24 |
| 6,760,945 B2 * | 7/2004 | Ferber et al. | 15/22.2 |
| 6,779,216 B2 * | 8/2004 | Davies et al. | 15/22.1 |
| 6,792,640 B2 * | 9/2004 | Lev | 15/28 |
| 6,895,625 B2 * | 5/2005 | Lev et al. | 15/22.1 |
| 2002/0124864 A1 | 9/2002 | Gross et al. | |

FOREIGN PATENT DOCUMENTS

| | | |
|---|---|---|
| CA | 81888 | 9/1997 |
| CA | 2323528 | 3/1998 |
| CA | 84252 | 7/1998 |
| CA | 86705 | 5/1999 |
| CA | 88711 | 1/2000 |
| CA | 89746 | 6/2000 |
| CN | 1103726 A | 6/1995 |
| CN | 1121687 A | 5/1996 |
| CN | 1252248 A | 5/2000 |
| CN | 1280806 A | 1/2001 |
| GB | 2059795 | 9/1997 |
| GB | 2098245 | 1/2001 |
| GB | 2105926 | 10/2001 |
| GB | 3004165 | 5/2002 |
| JP | 518985 | 8/1979 |
| WO | WO 96/31145 | 10/1996 |

OTHER PUBLICATIONS

Office Action for U.S. Appl. No. 10/237,902; dated Nov. 6, 2006.

* cited by examiner

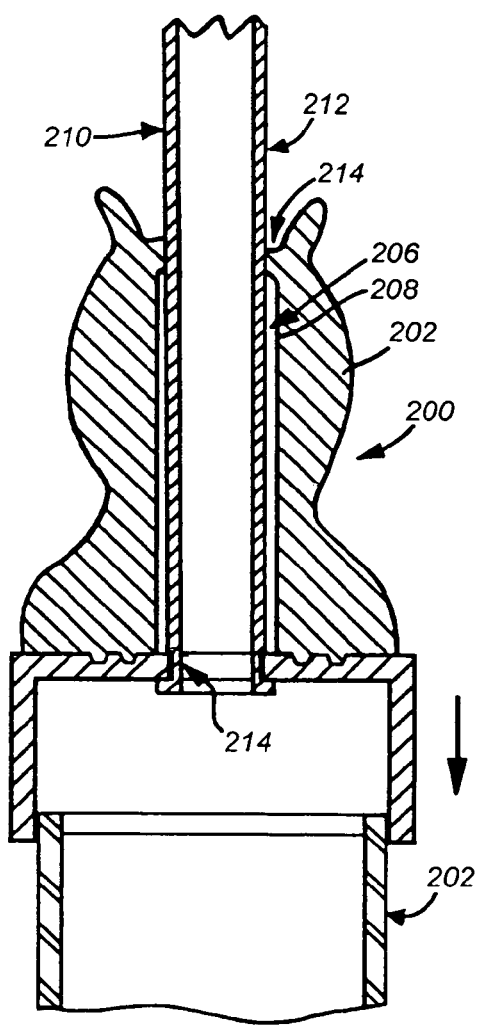
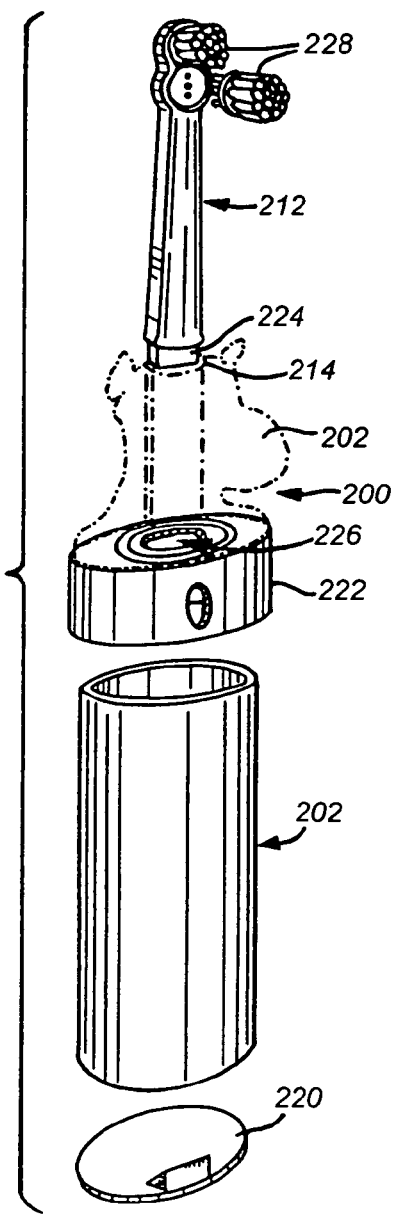
Fig. 6
Fig. 7

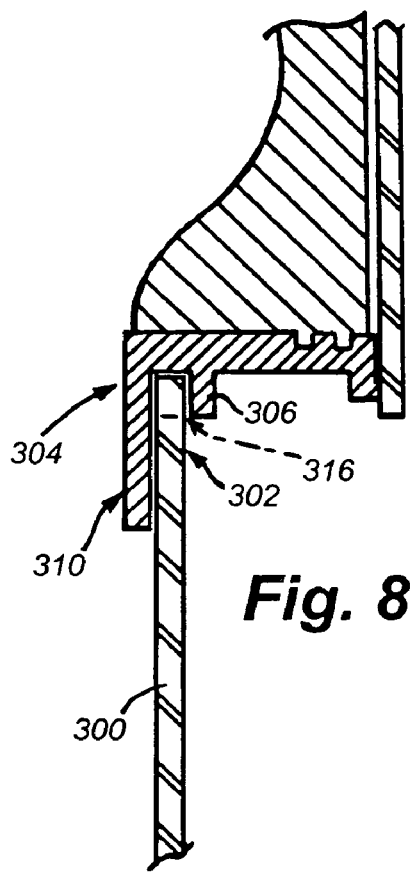
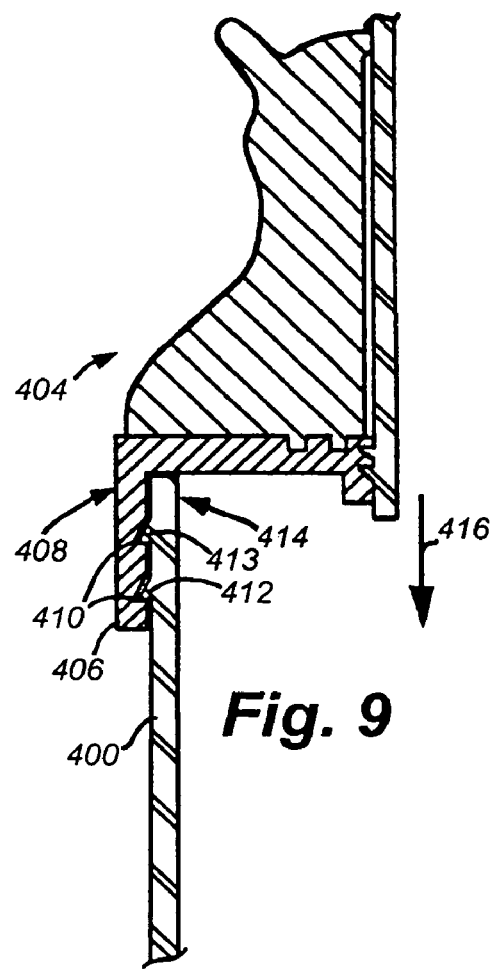

US 7,636,977 B2

TOPPER FOR POWER TOOTHBRUSH AND METHOD FOR FORMING THE SAME

CROSS REFERENCE TO RELATED APPLICATION

This is a continuation of application Ser. No. 10/237,902, filed Sep. 9, 2002, now abandoned the substance of which is incorporated herein by reference.

FIELD OF THE INVENTION

This invention relates to powered toothbrushes, and more particularly to decorations applied to powered toothbrushes and methods for attaching such decorations.

BACKGROUND OF THE INVENTION

Powered toothbrushes are becoming an increasingly desirable item for both adults and children. A variety of inexpensive semi-disposable and fully disposable powered toothbrushes are now available on the market. In order to interest children in developing good oral hygiene habits, many toothbrushes, including powered toothbrushes, are provided with decoration relevant to childrens' tastes. One of the more elaborate and desired forms of decoration is a sculpted feature applied to a portion of the brush handle. Such sculpted features can represent well-known cartoon characters or any other relevant three-dimensional subject matter including desirable toys.

The internal mechanism and case construction of powered toothbrushes varies widely. In general, all toothbrushes include a handle that contains the battery and a driving motor as well as a switch. Extending from the handle is a thinner, elongated shaft, that at its end includes one or more moving heads. Power is transmitted from the handle to the heads via various drive shaft arrangements. The cases of powered toothbrushes are formed from one or more pieces (shell halves) that are often joined together using adhesives, ultrasonic welding or other joining techniques. To incorporate a piece that represents a decorative feature (e.g., a cartoon character, toy etc.) it may be necessary to employ advanced construction and molding techniques. However, these techniques must not drive the cost of construction of the relatively inexpensive toothbrush too high or it will be uncompetitive in the mass market.

SUMMARY OF THE INVENTION

This invention overcomes the disadvantages of the prior art by providing a decorative piece in the form of a topper designed to seat at the base of the shaft and extending from the handle body of a power toothbrush. The topper is formed as a single molded piece on top of a base ring having a central hole that fits over the shaft and a lower skirt that mates with the handle. The base ring includes grooves or other indentations about the central hole that receive inflow from the topper when it is molded.

According to one embodiment, to construct the topper, the base ring is held in place with respect to the topper mold and molten (or otherwise-liquid) plastic is injected into the mold so that it fills the mold cavity and thereby flows into the indentations in the base ring, thereby securing the topper to the base ring when the decorative feature hardens sufficiently. The base ring and topper can then be slid over the shaft into a final mounted position on the assembled brush.

In another embodiment the handle body can be sealed using an outer cover or sleeve. This cover or sleeve can be seamless about its circumference and open at one end while closed at the bottom end. In this manner a 360° label/decal, such as a heat-transferred label/decal can be applied to the sleeve.

BRIEF DESCRIPTION OF THE DRAWINGS

The invention description below refers to the accompanying drawings, of which:

FIG. 6 is a front cross section of an assembled topper and a base ring on a brush shaft detailing the seal between the shaft and the topper;

FIG. 7 is an exploded perspective view of the assembly of a topper onto an exemplary toothbrush according to another embodiment of this invention;

FIG. 8 is a cross section of a technique for engaging the base ring onto a handle body of a power toothbrush according to an embodiment of this invention; and FIG. 9 is a cross section of a technique for engaging a base ring onto a handle body of a toothbrush according to an embodiment of this invention.

DETAILED DESCRIPTION OF THE INVENTION

Figure 1:
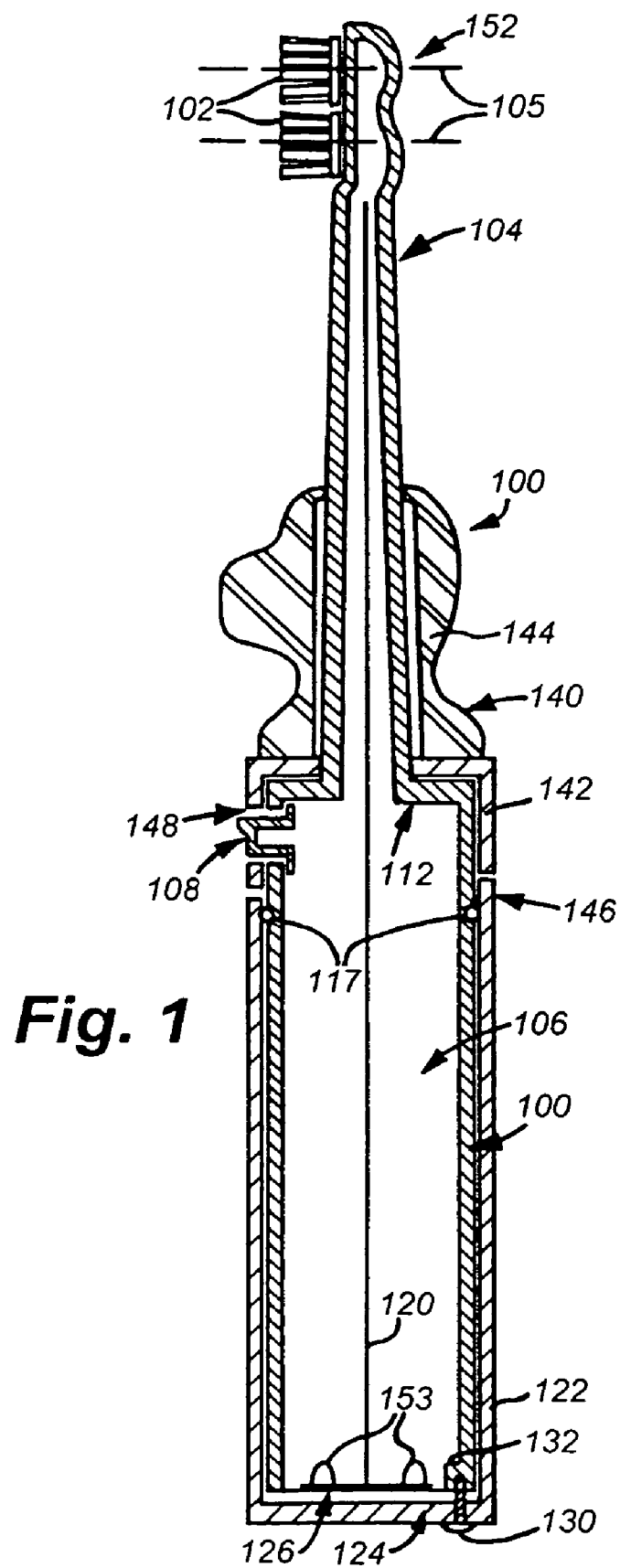
FIG. 1 is a side cross section of an assembled power toothbrush with an exemplary topper placed thereon according to one embodiment.

FIG. 1 shows a side cross-section of an exemplary powered toothbrush 100 according to an embodiment of this invention. The featured toothbrush includes a unique dual head 102 assembly at the end of a hollow toothbrush shaft 104. For the purposes of this illustration, the internal mechanism of the toothbrush has been removed. In general, such a mechanism can include a drive shaft passing through the hollow shaft 104 to drive the toothbrush heads 102 in a continuous or reciprocating motion about respective rotational axes 105. A motor, gearing and battery (not shown in FIG. 1) are positioned within the main body interior cavity 106 of the toothbrush, which also acts as a handle. The size of the main body handle, and its shape, can be designed to accommodate the hand of an adult or a small child as appropriate. The toothbrush is activated by an exposed button 108 that can have both momentary contact and continuous-on functions. In the illustrative embodiment, the shaft is formed integrally with the inner handle body 110. A top step 112 is provided between the shaft and the handle body 110.

Figure 2:
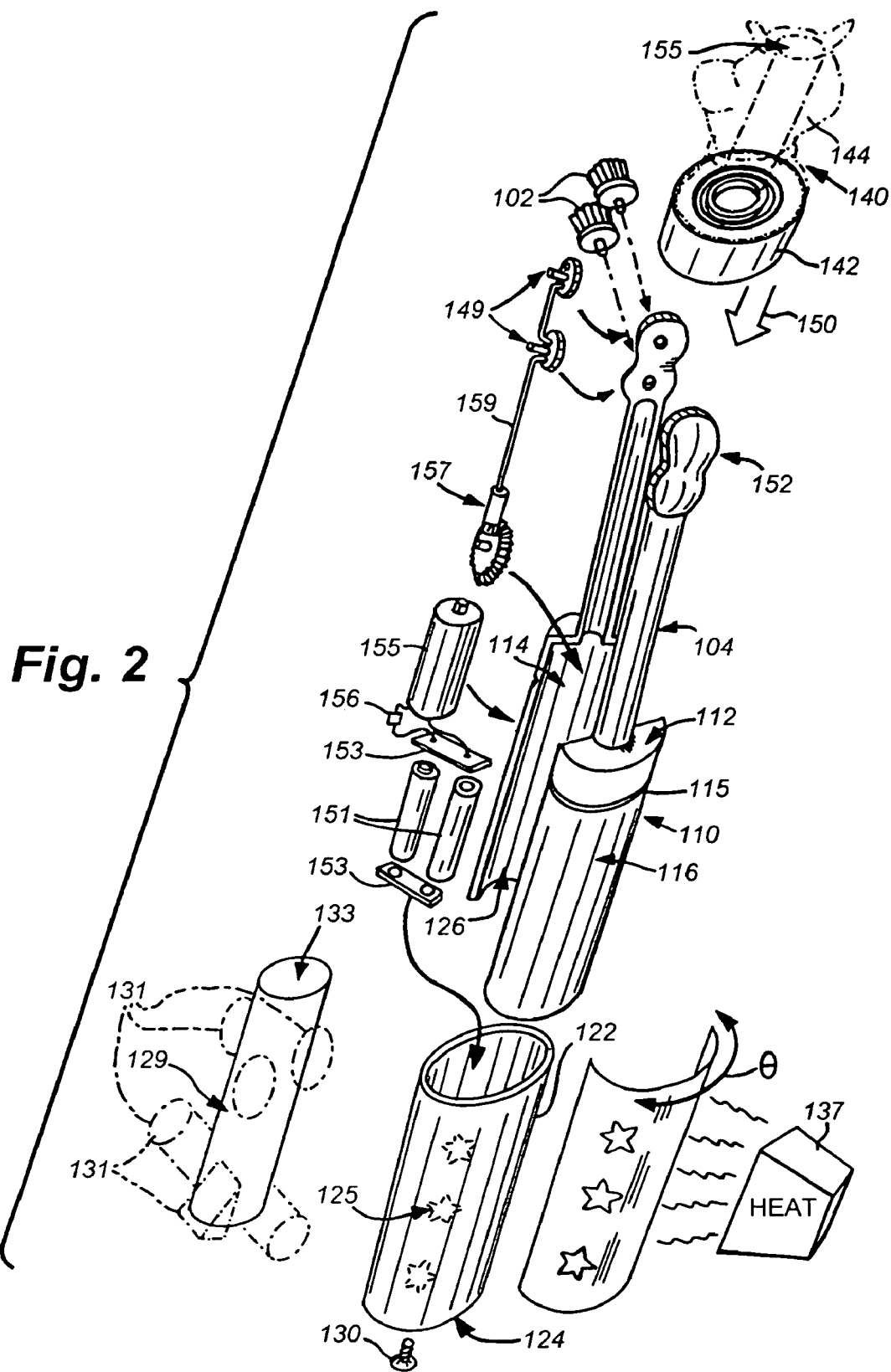
FIG. 2 is an exploded perspective view of the toothbrush of FIG. 1.

With reference also to FIG. 2, the shaft 104 and handle body 110 are formed as separate shell halves 114 and 116 in this embodiment. The halves are joined along a seam line using appropriate adhesives, welding or fasteners. In this embodiment, an outer handle cover or sleeve 122 is also provided. The handle cover includes a bottom 124 that seals the hollow opening 126 in the bottom of the handle 110. The cover 122 can include a variety of shapes and/or graphic patterns 125 thereon. Likewise, the handle cover can be formed as a more complex outer shape such as a car body or other desirable shape 129. The sculpted features 131 (shown in phantom) of the complex sleeve shape are built up from an internal cavity shape 133 that conforms to the shaped of the handle body 110.

Notably, where a straight cylindrical (for example, circular, polygonal or elliptical cross section) sleeve is employed (exemplary sleeve 122), the ability to construct the sleeve as a seamless cup allows the inner seam of the shell halves 114 and 116 to be obscured and a desirable "360 degree" (θ) decal 135 to be applied using heat transfer 137 or other techniques. The resulting finished graphic appears very smooth and essentially seamless, wrapping around the entire perimeter of the cover or sleeve 122. It is removably secured to the body 110 using a screw 130 that threads into a dog 132 near the opening 126. A variety of other securing techniques can be employed. In addition, in an alternate embodiment, the outer sleeve or cover 122 can be omitted and a cap or hatch (see for example FIG. 7) can be used to secure the opening 126. Batteries (see FIG. 2) are provided through the opening and appropriate connector contacts (153) can be provided at the bottom 124 of the cover or sleeve 122. Note that the sleeve can be sealed against liquid infiltration using an appropriate sized O-ring 117 (FIG. 1) seated within a circumferential cutout 115 (FIG. 2) on the upper end of the body handle wall 110. This O-ring 115 seals against the inner wall of the sleeve, thus ensuring that the internal mechanism and batteries remain free of contamination by water or foreign debris (e.g. toothpaste, plaque, etc.).

As a further decorative feature, the toothbrush of this invention includes a topper 140 mounted over the body handle shoulder 112 and surrounding the lower portion of the shaft 104 adjacent to the shoulder 112. The topper 140 includes a base ring 142 and the decorative character or feature 144 extending upwardly away from the base ring 142. Note that the base ring is sized so that it is essentially flush with the upper end 146 of the sleeve or cover 122. In addition, the base ring includes a hole 148, through which is received the button 108. The hole may be enclosed on all sides, or may be formed as an open mounting of the ring 142 onto the body shoulder 112 during assembly.

With further reference to FIG. 2, the assembled base ring 142 and feature 144 of the topper 140 are assembled onto the toothbrush, in this embodiment, by sliding them over (arrow 150) the distal end 152 of the shaft 104. In general, the sliding action occurs before the heads 102 are applied to their internal drive gearing and axles 149 (shown schematically), but after the halves 114 and 116 of the shell are joined together with the mechanism (battery 151, contacts 153, motor 155, switch 156, gearing 157 and driver shaft 159) (shown schematically) sandwiched between the pre-assembly shell halves 114 and 116. The ring 142 is slid downwardly along the shaft until it seats around the body 110 and firmly against the shoulder 112. Note that the topper includes an axial through-hole 155 to facilitate sliding along the shaft. The details of the shape and size of this hole are described further below.

Figure 3:
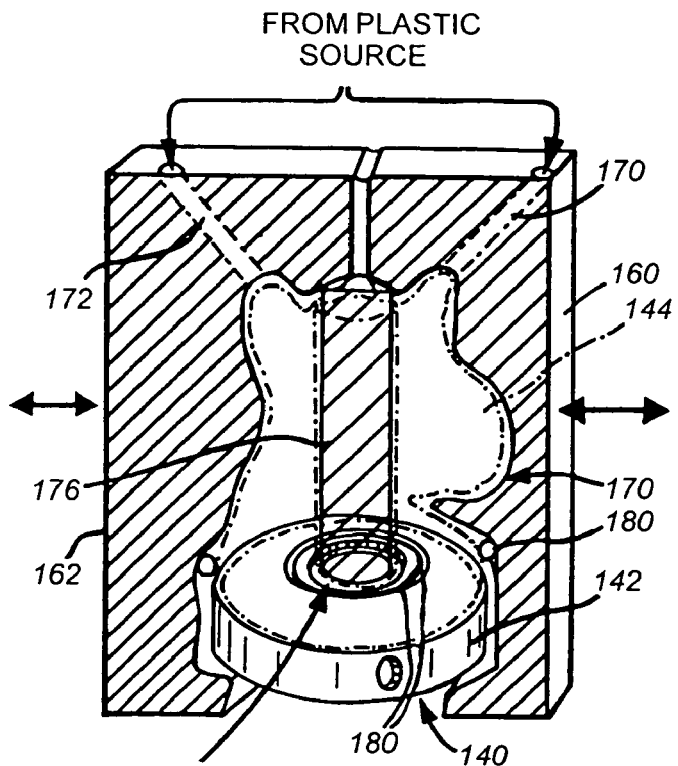
FIG. 3 is a partial perspective view of a topper base ring and decorative feature being formed in a mold according to an embodiment of this invention.

In accordance with the unique topper arrangement of this invention, FIG. 3 details a schematic mold for constructing a decorative feature 144 (shown in phantom) on top of the ring 142. It should be noted that the ring of this embodiment is typically formed from the same material as the body shell. For example, the material can be a rigid plastic such as ABS or polystyrene. The feature 144 is typically constructed from a softer plastic such as SEBS or TPU TPE (i.e. a soft polyvinylchloride (PVC)). In accordance with FIG. 3, two or more mold halves 160 and 162 are joined around an already completed base ring 142. The mold halves each include an associated injection channel 170 and 172 through which molten or otherwise liquefied plastic is injected. The cavity 170 defines a negative of the shape of the feature. A mandrel or other cylindrical member 176 is provided at the center of the feature and through a hole 178 in the base ring 142 in order to maintain the axial through-hole (155) described above. In one embodiment, the mandrel can be inserted through the bottom of the base ring and can be removed after the forming of the feature is complete. A seal 180 prevents plastic from escaping from the base ring.

Figure 4:
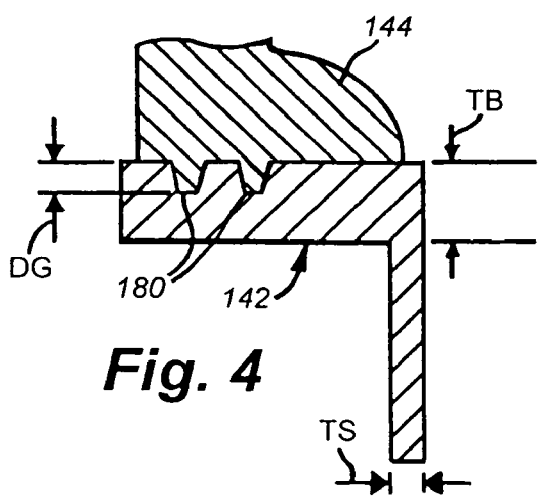
FIG. 4 is a more detailed side cross section of the engagement of the topper decorative feature of FIG. 1 with the base ring.
Figure 5:
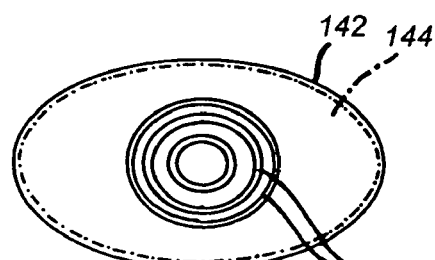
FIG. 5 is a top view of an exemplary decorative feature of FIG. 1 in engagement with the base ring.

Referring also to FIGS. 4 and 5, the base ring 142 includes two or more concentric grooves 180. The grooves 180 are designed to provide additional holding area for the plastic feature 144. When the feature 144 is molded, the adhesive properties of the plastic tend to join it firmly to the ring 142. The joint is further reinforced by the flow of plastic into the grooves 180. In one embodiment, the grooves have a depth DG of approximately 0.04 inch. The overall thickness TB of the top of the base ring 142 is approximately 0.11 inch and the thickness TS of the side skirt of the base is approximately 0.08 inch. Likewise, the thickness of the outer cover 122 can be approximately 0.08 inch.

In this embodiment, the grooves 180 are shaped as inwardly tapering wedges (in cross section). However, a variety of shapes can be formed including a square or rectangular cross section, a curved/semi-circular cross section or even an undercut dovetail-shaped cross section. In addition, while two concentric semi-circles are employed in this embodiment, it is contemplated that more or fewer groove formations can be employed. Likewise, the formations need not be circular, but can be ellipse-shaped, rectangular or any appropriate irregularly-sized shape. In addition, while continuous, unbroken grooves are used according to this embodiment, the term(s) "groove" or "grooves" should be taken broadly to include a variety of broken structures including segmented grooves or even a plurality of individual holes. In general, any formation on the surface of the base ring that facilitates greater gripping of the feature when it is molded onto the base ring is contemplated as a "groove" according to this invention using the above formation approach no additional adhesive is required between the feature and base ring. Note that the size of the feature's contact surface with respect to the base ring top is highly variable. That is, the feature can contact a relatively small area with respect to the total area of the base ring. Likewise, the feature can contact virtually the entire top surface of the base ring. The top surface grooves are adapted in size, shape and layout to accommodate the desire contact surface profile.

It is also expressly contemplated that the base ring and its associated top surface can be irregular or sculpted in shape. The top surface need only enable liquid plastic to be laid thereupon for joining upon hardening. In addition the feature may extend outwardly to a width/diameter that is significantly greater than the top surface's perimeter.

The FIG. 6 illustrates the topper assembly 200 mounted on a handle body 202 according to an alternate embodiment. Before discussing in detail the topper assembly 200, the feature 202 will be discussed in further detail. This discussion applied generally to the above-described feature 144 and any other feature to be employed according to an embodiment of this invention. The feature 202 includes a central axial hole having a gap 206 along its length formed between the inner wall 208 of the hole and the outer wall 210 of the toothbrush shaft 212. In one embodiment, the gap can be approximately 0.015 inch. This gap ensures that when the feature is passed over the shaft, or (as described below) the shaft is passed over the feature, that it is not bound by excessive friction. In order to ensure an appropriate seal and a secure friction fit between the outer wall 210 of the shaft 212 and the feature 202, an upper lip 214 is provided at the top end of the feature 202. The upper lip has an inner diameter that, in a free-unattached state, is slightly smaller than the outer diameter of the shaft 212 in the region of final fitment between the shaft and feature. Note that the shaft may be tapered, and thus, its outer diameter may vary along its length—accordingly, the lip inner diameter is sized with the taper in mind. Since the decorative topper feature 202 is formed from a pliable plastic in this embodiment, slight deformation at the lip 214 is accommodated as the shaft and feature slide with respect to each other into a final fitment. It is, of course, contemplated that the topper feature can be formed from more rigid material. In such an instance, a lip can be formed to include a sealing member, such as an O-ring.

With further reference to the alternate embodiment shown in FIG. 6, an exploded view is shown further in FIG. 7. In this embodiment, the handle body 202 is a separate member formed as an elliptical cylinder with an open top and bottom. As noted above, the bottom may be covered with an overriding case or by a cap. The topper 200 includes a base ring 222 and feature 202 that are constructed as described generally above with reference to FIGS. 1-5. In this embodiment, the toothbrush shaft 212 is formed as a separate member from either a single molded piece or a pair of shell halves. At the base of the toothbrush shaft 212 is formed a plug 224 having a smaller diameter than the main body of the shaft 212. The plug is sized and arranged to fit within a socket hole 226 formed in the top of the base ring 222. The plug and socket can be joined together permanently using a locking mechanism, adhesives, welding or any other acceptable joining technique. When joined together, the topper lip 214 seals against the outer wall of the main body of the shaft to prevent infiltration of water and to provide a secure friction fit of the shaft with respect to the topper. In an alternate embodiment, the shaft can be constructed in a manner that allows it to be slid out of the topper with associated components, such as the drive shaft. In this manner, a mechanism for enabling the shaft to be changed when the brush heads 228 is exhausted. A releasable locking mechanism or a simple friction fit can be used to secure the shaft in such an alternate embodiment.

With reference finally to FIGS. 8 and 9, two alternate techniques for joining the base ring of the topper assembly to a handle body are shown. These techniques are applicable to either of the embodiments described above. In FIG. 8, the handle body 300 includes a basic opening region 302. The topper assembly 304 includes an inner securing wing 306 that bears against the inner wall of the handle body 300. In addition, the outer skirt 310 of the base ring faces the outer wall of the handle body 300. Adhesive 316 can be applied between the guide ring 306 and the inner wall, or at another location within the "sandwich" between the guide ring 306, handle body 300 and skirt 310. This adhesive can be sufficient to seal the structure against water infiltration. Additional sealing fixtures, such as O-rings (not shown) can also be provided.

FIG. 9 shows an alternate embodiment for securing the handle body 300 and topper assembly 404 together. In this embodiment, the side skirt 406 of the base ring 408 includes a pair of circumferential (or segmented) triangular indentations 410. These indentations are sized and arranged to mate with corresponding triangular cross section formations 412 on the top end 414 of the body handle 400. The orientation of the formations 412 and interlocking indentations 410 is such that when downward pressure (arrow 416) is applied to the base ring with respect to the body handle 400, the skirt 406 deforms sufficiently to cause the indentations 410 and formations 412 to interlock. This firmly secures the base ring 408 to the body handle 400. Additional sealing mechanisms such as an O-ring can also be provided between the top portion 414 of the body handle 400 and the base ring 408 to further enhance the seal therebetween.

The foregoing has been a detailed description of the illustrative embodiments of the invention. Various modifications and additions can be made without departing from the spirit and scope of this invention. For example, the materials used for various parts can be widely varied. The internal mechanism and/or number of brush heads used can vary. In addition, the movement pattern of the brush heads can be varied from the depicted rotational movement about rotational axes. Finally, it is contemplated that the size, shape and style of the topper feature as well as the shape of the handle can be widely varied from that depicted. In other words, large toppers having varied sizes can be employed and the handle can include non-cylindrical shapes including tapered shapes, sculpted shapes, rectangular-cross section shapes, and the like. Finally, while the topper and techniques described herein are directed generally toward a powered toothbrush, the topper can also be used in conjunction with a non-powered toothbrush having an appropriately sized and shaped handle. The teachings herein are expressly contemplated to include such brushes. Accordingly, this description is meant to be taken only by way of example and not to otherwise limit the scope of the invention.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A power toothbrush comprising:
 a body handle comprising a shell having a length between an upper and lower ends thereof and parallel to a longitudinal axis of the toothbrush the shell formed by two separate convex shell halves having solid and relatively thin walls, the shell halves being joined together at their respective mating surfaces comprising thickness of the walls of the shell halves and forming a seam line extending alone the entire length of the shell, the shell circumferentially encasing at least one battery, a motor and gearing connected to the motor, and having the lower end that is open to removably receive the at least one battery;
 a shaft extending from the upper end and having, at a distal end thereof, a moving brush head assembly;
 a drive shaft, extending from the gearing through the shaft to the brush head assembly, adapted to move the brush head assembly; and
 a seamless covering sleeve constructed and arranged to pass over the lower end of the body handle and into an engaged position on the body handle, including a bottom that retains the battery in the body handle; and a topper assembly seated over the shaft in engagement with the body handle and adjacent to an upper end of the sleeve when the sleeve is in the engages position.

2. The power toothbrush as set forth in claim 1 wherein the topper assembly includes a sculpted decorative feature and a base ring, the base ring having a skirt extending below the shaft along the body handle.

3. The power toothbrush as set forth in claim 2 wherein the skirt includes a cutout for a switch.

4. The power toothbrush as set forth in claim 1 wherein the sleeve includes a decal having a decorative pattern that extends about a perimeter of the sleeve.

5. The power toothbrush as set forth in claim 4 wherein the decal comprises a heat transfer decal.

6. The power toothbrush as set forth in claim 1 wherein the lower end of the body handle includes a dog for receiving a screw that passes through the bottom of the sleeve and is adapted to secure the sleeve in the engaged position.

7. The power toothbrush as set forth in claim 1 wherein the body handle includes a circumferential sealing ring that engages an inner wall of the sleeve when the sleeve is in the engaged position.

8. The power toothbrush as set forth in claim 1 wherein the bottom of the sleeve includes a battery contact for interconnecting a plurality of batteries.

* * * * *